United States Patent [19]

Brisson

[11] 4,322,594
[45] Mar. 30, 1982

[54] TEMPERATURE CONTROL SYSTEM WITH ALARM AND SHUT DOWN FOR NON-TRACKING CONDITION OF DUAL THERMOMETERS

[75] Inventor: A. Glen Brisson, Arlington Heights, Ill.

[73] Assignee: Respiratory Care, Inc., Arlington Heights, Ill.

[21] Appl. No.: 163,485

[22] Filed: Jun. 27, 1980

[51] Int. Cl.³ .............................................. H05B 1/02
[52] U.S. Cl. .................................. 219/497; 219/506; 219/499; 219/509; 128/724; 128/736
[58] Field of Search ............... 219/497, 499, 501, 251, 219/510, 509, 511, 506; 307/117; 128/724, 736

[56] References Cited

U.S. PATENT DOCUMENTS 3,903,883  9/1975  Pecina et al. ......................... 219/497
3,982,098  9/1976  Trostles ............................... 219/501

FOREIGN PATENT DOCUMENTS 2809089  9/1979  Fed. Rep. of Germany ...... 219/497

Primary Examiner—Roy N. Envall, Jr.
Assistant Examiner—M. Paschall
Attorney, Agent, or Firm—Eric P. Schellin

[57] ABSTRACT

In a system in which temperature control of a heated region is critical, assurance means of fail-safe nature are provided to guard against improper temperature. An example wherein temperature is critical is: the artificial ventilation of an unconcious patient's lungs by periodically inspired heated gas under pressure. The assurance means includes dual thermometers which sense the actual temperature in the heated region. The actual temperature is compared with the desired temperature to control an electric heater, which, when energized, increase the temperature of the heated region. Furthermore, the temperatures, as sensed by the two thermometers, are compared with each other. If the difference exceeds a predetermined limit, an alarm is given and the heating system is shut down.

8 Claims, 5 Drawing Figures

4,322,594

TEMPERATURE CONTROL SYSTEM WITH ALARM AND SHUT DOWN FOR NON-TRACKING CONDITION OF DUAL THERMOMETERS

RELATED APPLICATION

This application is based on a further development of the invention disclosed in prior appication Ser. No. 89,320, filed Oct. 30, 1979, by means of which a fail-safe feature is added. The fail-safe feature is not restricted to such use, but is of general utility.

THE DRAWINGS

SUMMARY

Electric heating temperature control systems utilize temperature sensing means to control the heating. Thermistors are often used as the temperature sensing means since they have a steep resistance versus temperature characteristics, which permits the use of control circuits having lesser amplification than would be required if, say, a thermocouple or a platinum resistance thermometer were used. Thermocouples are midway, in sensitivity, between thermistors and platinum resistance thermometers. However, thermistors, comprising a composition, are not as stable as thermocouples and thermocouples are not as stable as a platinum resistance thermometer. That is, the thermistor (or thermocouple) can drift, with the result that the control circuitry stabilizes and nulls the circuit when an improper temperature has been achieved.

Drift in an electric temperature control system is not always acceptable. For example, when an unconscious non-breathing patient is kept alive in an intensive care unit by having a warmed air-oxygen-moisture mixture periodically forced into his lungs through an intubation tube, lodged air-tight in his trachea by means of an inflated cuff, it is imperative that the ventilating mixture be at a predetermined temperature. A departure from that temperature could be life-threatening.

Accordingly, a fail-safe assurance means is added to an electric temperature control system whereby, when the controlled temperature drifts away from its predetermined value, an alarm is given and the electric heating system is deenergized.

The fail-safe assurance means utilizes a pair of temperature sensors, located adjacent each other in the heated zone, to sense the temperature of the same locus. If the temperature sensors are operating correctly, the resulting electric signals, indicative of temperature, should be either identical or within a tolerance range from each other. The difference, if greater than the tolerance, is used to raise an alarm and shut down the electric heating system.

DETAILED DESCRIPTION

Figure 1:
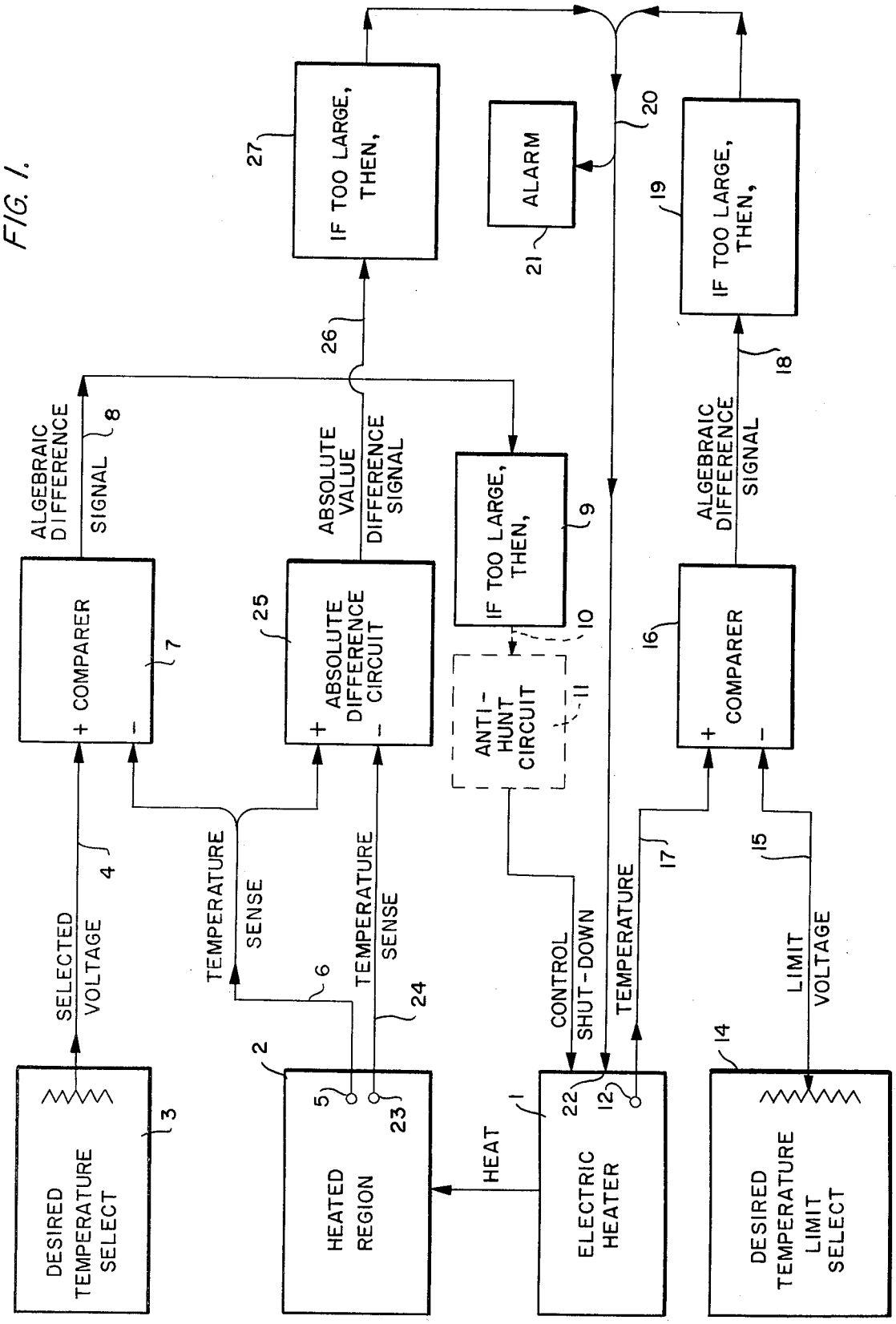
FIG. 1 is a box diagram showing how the logic of the temperature control system operates.

The block-diagram of FIG. 1 sets forth the concept behind the invention. An electric heater 1 supplies heat to a heated region 2. The desired temperature is set in adjustor 3 to produce a selected voltage, indicative of the desired temperature, on conductor 4. A temperature sensing means 5 in the heated region produces a voltage on conductor 6 indicative of the actual temperature. The voltages on conductors 4 and 6 are subtracted in comparer 7 to produce an algebraic difference signal on conductor 8. The said signal is an algebraic one because the sign of the signal indicates whether the voltage on conductor 4 is more positive than that on conductor 6, or vice versa.

The algebraic difference signal is applied to the amplitude responsive circuit 9 to produce an output on conductor 10 which controls the operation of electric heater 1. An anti-hunt circuit 11 may be provided when the electric heater or the heated region has a high thermal inertia. The control of electric heater 1 over the feedback logs 7, 8, 9, 10 and 11, as thus described, is in accordance with well known practice and need not be further elaborated.

The electric heater 1, when everything is working properly, will be running at a higher temperature than desired for the heated region 2, since heat flows from the heater 1 to the heated region 5 only because of a temperature difference. However, if electric heater 1 gets very hot, something is wrong, as normally the electric heater is only moderately hotter than the heated region.

Accordingly, a temperature limiting system is provided to limit the maximum temperature of the heater itself. This comprises a temperature sensing means 12 which is built into the electric heater itself. An adjuster 14 produces a voltage indicative of the permissible temperature limit on conductor 15, and this voltage is subtracted from the voltage on conductor 17, the voltage of which is indicative of the temperature of the electric heater 1. The voltages on conductors 15 and 17 are compared in comparer 16. The resulting algebraic difference signal appears on conductor 18, and is applied to amplitude circuit 19, which produces an output on shut-down conductor 20. When an output appears on shut-down conductor 20, an alarm 21 is activated and the electric heater 1 is disconnected from its energy source by the input control at 22.

In order to give fail-safe assurance that the temperature of heated region 2 is at the desired temperature, the temperature sensing means 5, previously described, is duplicated at 23. Temperature sensing means 5 and 23 are closely adjacent and will therefore sense the same temperature. If all is well, the voltage, indicative of temperature, on conductor 6 will be identical to that on the corresponding conductor 24. If one of the temperature sensing means 5 or 24 has drifted from its original characteristic, then the voltages on conductors 6 and 24 will differ. The voltages on conductors 6 and 24 are applied to absolute difference circuit 25 to produce on conductor 26 a voltage which increases monotonically from zero with either a positive or negative departure from zero of the difference in the voltages on conductors 6 and 24.

Thus, if one of the temperature sensing means drifts and the other is stable, it does not matter whether it is 5 or 23 which drifts, and it does not matter whether the drift is positive or negative—in any of these instances, the voltage on conductor 26 is a measure of the drift. That voltage is applied to amplitude circuit 27, and, if too large, will produce an output which appears on shutdown conductor 20 to activate alarm 21 and cut off the electric heater 1 at 22.

Figure 2:
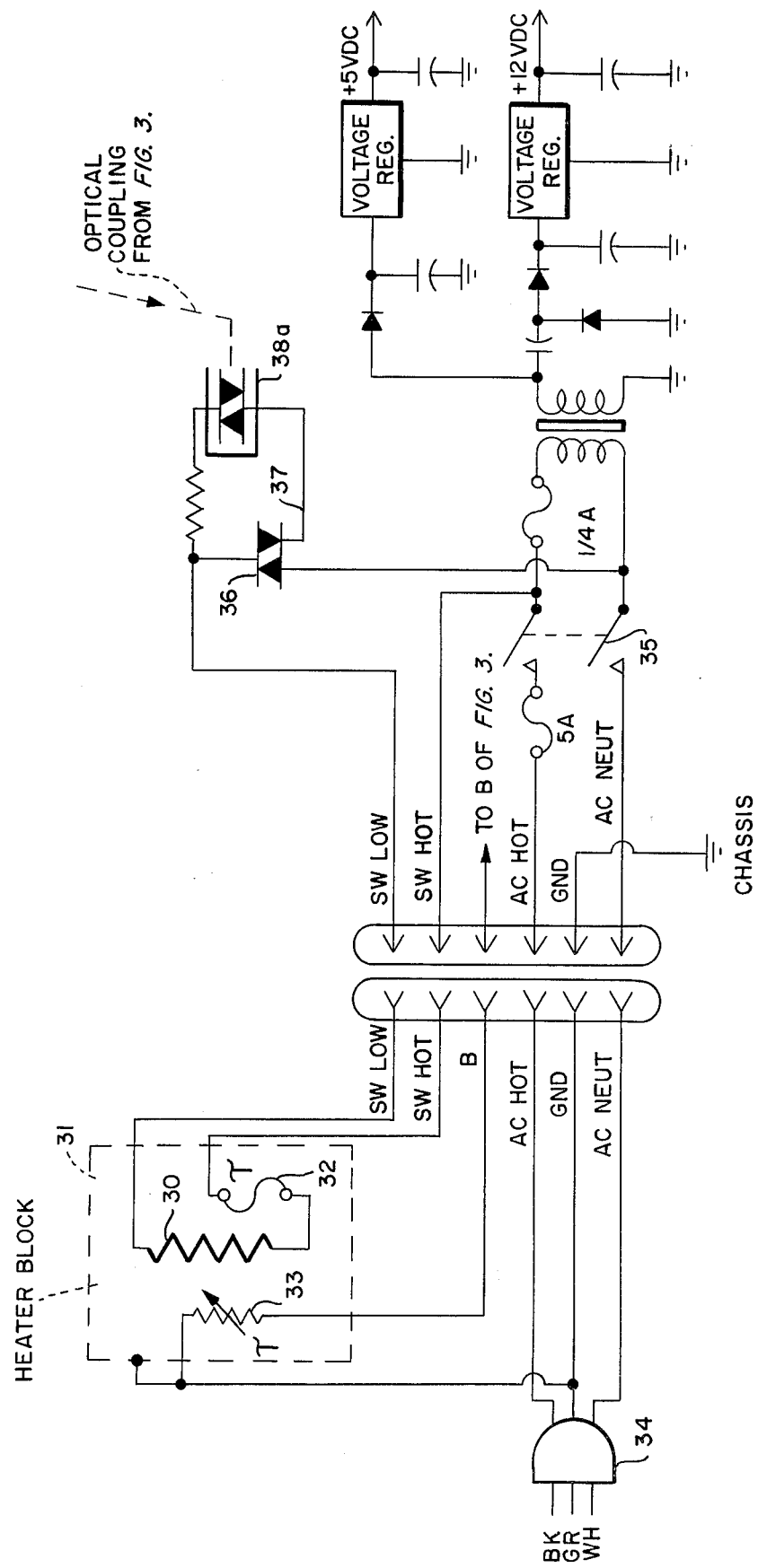
FIG. 2 is a circuit diagram of the heater resistor energizing and deenergizing portion of the system.
Figure 3:
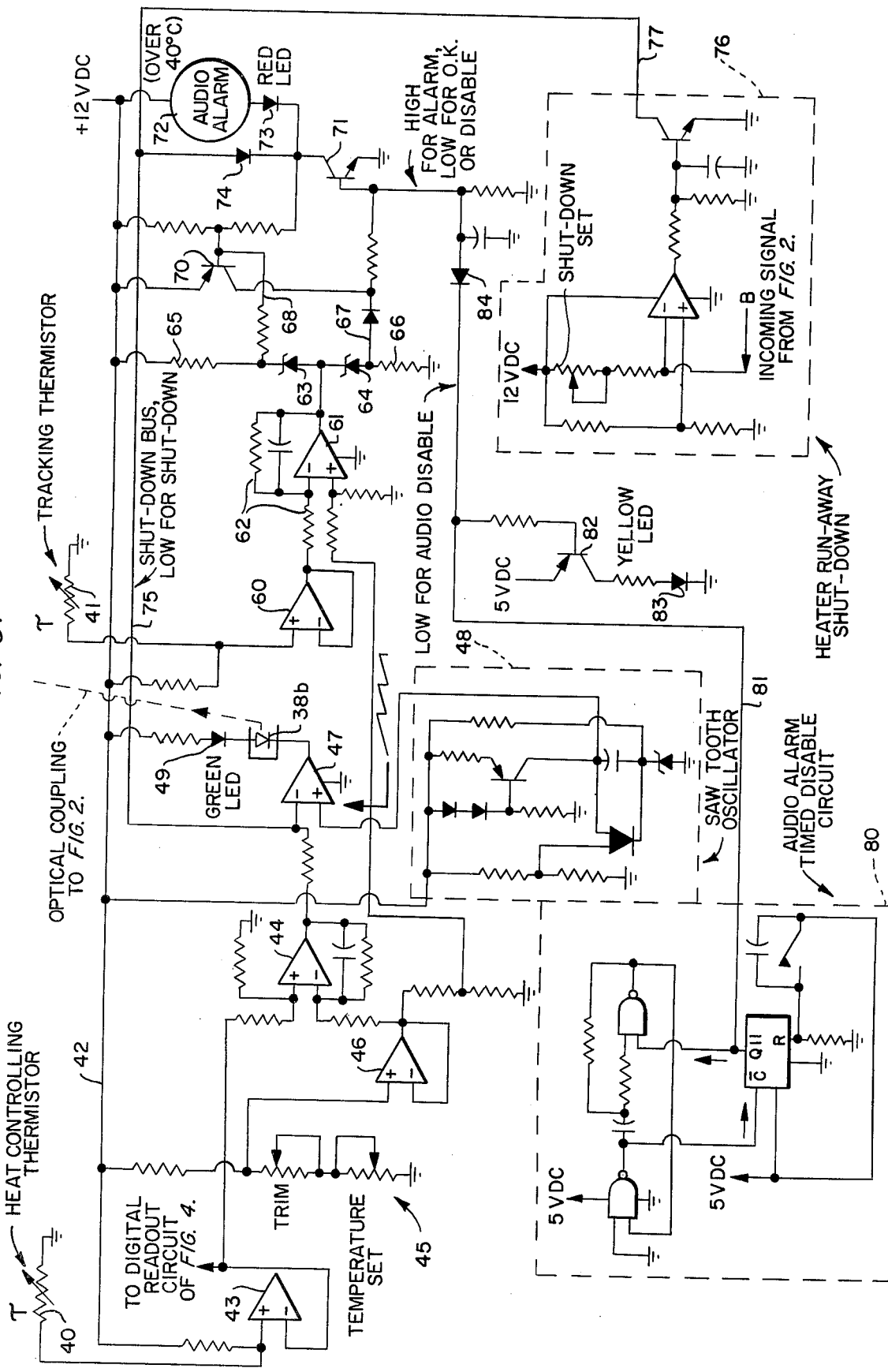
FIG. 3 is a circuit diagram of the portion of the system which responds to temperature to control the heater energization and deenergization portion of the system. Included in FIG. 3 is the tracking, runaway and shut down circuitry which ensures fail-safe operation.
Figure 4:
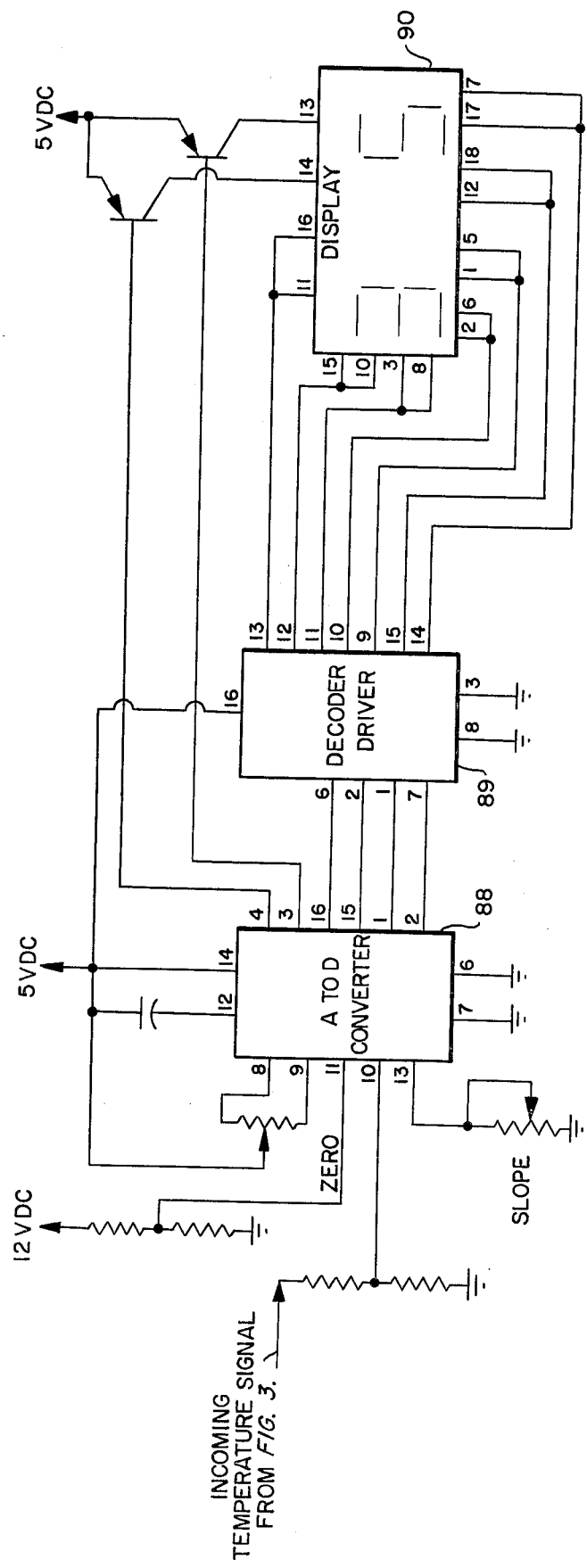
FIG. 4 is a circuit diagram of the digital read out circuitry which displays the value of the temperature.

An exemplary wiring diagram of one embodiment of the invention is seen in FIGS. 2, 3 and 4. These Figures must be read together, as each shows a portion of the circuit. The way the Figures are interconnected will be apparent, especially from the legends, to those skilled in the art.

In FIG. 2 the heater resistor 30 is encased in a heater block 31, which also includes thermal fuse 32 and thermistor 33. The heater resistor 30 is energized from electric power plug 34 through an obvious circuit, including on-off switch 35 and triac 36. The triac 36 is a four layer PNPN device which normally is non-conducting to the AC voltage, but can be triggered by its gate 37 to be conductive. When heat is called for by the control system, to be described, the gate is pulsed once during each cycle of the alternating current by optically coupled triac 38a, which is activated by its integral light emitting diode 38b of FIG. 3. Thus, when the LED 38b lights up, triac 38a becomes conductive, which puts the required voltage on gate 37 of triac 36 needed to render the triac 37 conductive. This energizes the heater resistor 30.

Should the heater resistor 30 run away through some malfunction, the excess temperature is sensed be thermistor 33, which reduces its resistance between terminal B and chassis ground, to activate a shut-down circuit in FIG. 3, to be described. Should the heater resistor continue to increase further in temperature, the thermal fuse 32 will blow, completely disconnecting the heater resistor from electric power. The remainder of the circuitry of FIG. 2 relates to the bias power supplies, which need not be further described, being conventional.

In FIG. 3 there are two thermistors, corresponding to the temperature sensing means 5 and 23 of FIG. 1. Thermistor 40 controls the intermittant energization of heater resistor 30 of FIG. 2 while thermistor 41 is a tracking thermistor to sense excessive drift in the characteristics of the thermistor.

Thermistor 40 receives a bias current through an obvious circuit from bias supply conductor 42. As the temperature rises, the resistance of thermistor 40 falls, so the positive voltage at the output voltage follower amplifier 43 is inversely related to temperature. This output is directly utilized to control the digital temperature read-out indicator of FIG. 4, to be described. This output is also applied to the non-inverting input of differential amplifier 44, wherein it is compared with the voltage supplied by the temperature setting potentiometer 45 and voltage follower 46.

The voltage output of differential amplifier 44 is applied to the inverting input of differential amplifier 47.

Differential amplifier 47 is not supplied with any feedback circuit, and its gain is very large. Therefore, the output of differential amplifier 47 will tend to go to the extreme voltages of the bias supply or chassis ground, since the output will either saturate or be cut off when the two inputs are not almost identically equal.

It will be seen that, as the temperature of thermistor 40 climbs, the output of differential amplifier 47 has a tendency to go positive.

The non-inverting input of differential amplifier 47 is supplied with a saw tooth wave by saw tooth oscillator 48. The output from differential amplifier 47 will therefore be a pulse-width modulated pulse wave whose positive excursions will be of greater duration when the thermistor 40 is warmer.

When the output of differential amplifier is high, the voltage of the output will buck the bias voltage supply conductor 42 and the light emitting diode 38b will go out. LED 38b controls triac 38a of FIG. 2 and ultimately the heating of heater resistor 30.

It will be seen that the pulse-width modulated output of differential amplifier 47 makes the feedback system described a proportional control type, in which the correction applied is proportional to the departure sensed. Such a system, especially when the thermal inertia of the heater block 31 is low, is much freer from unwanted cycling and hunting than would be a system not using proportional control, such as an all heat on or all heat off system.

A green light emitting diode 49 is energized whenever the heater resistor 30 is energized. LED 49 thus winks on and off, at the frequency of the saw tooth oscillator 48, whenever the system is operating in a stable state.

Tracking thermistor 41 receives a bias current through an obvious circuit from bias supply conductor 42, and controls the voltage applied to the inverting input of differential amplifier 61 through voltage follower 60. This voltage is compared in differential amplifier 61 with a voltage, derived from temperature setting potentiometer 45, which is applied to the noninverting input. The resulting output of differential amplifier 61 is a voltage which varies linearly with the departure of the temperature sensed by thermistor 41 from that set by the temperature setting potentiometer 45. The steepness of the output characteristic slope is determined, in part, by the value of the feedback resistors 62, which will in turn affect the sensitivity of the tracking alarm, to be described.

The output of differential amplifier 61 is applied to the midpoint of a signal drift detector comprising a voltage divider which includes identical Zenner diodes 63 and 64 and identical resistors 65 and 66. The Zenner diodes each have a breakdown voltage of slightly more than half of the voltage on bias supply conductor 42.

Accordingly, when the output voltage of differential amplifier 61 is midway between the bias voltage and ground, neither of the Zenner diodes 63 or 64 will conduct. If the output of differential amplifier 61 goes more positive, Zenner diode 64 conducts, causing conductor 67 to go positive; if the output goes more negative, Zenner diode 63 conducts, causing conductor 68 to go more negative.

Bearing in mind the phase inversion from base to collector of transistor 70, it is apparent that either the just mentioned negative going voltage excursion on conductor 68 or the just mentioned positive going voltage excursion on conductor 67 will cause transistor 71 to conduct, thereby causing the audio alarm 72 to sound and the red light emitting diode 73 to light up.

Thus, if the output voltage of differential amplifier 61 wanders significantly from a value half way between bias voltage and chassis voltage, the signal drift detector will cause the audio alarm 72 to sound.

When the audio alarm 72 sounds, the red LED 73 will signal "danger". Furthermore, the low voltage at the collector of transistor 71 will, through diode 74, pull down the voltage of shut down bus 75, thereby turning off the electric heat at the inverting input of differential amplifier 47 through the same optical control switch 38 as hereinbefore described.

In the event there is a heat runaway, the thermistor 33 of FIG. 2 will signal run-away circuit 76 of FIG. 3 to cause a low output on conductor 77. This also will pull down the potential of shut down bus 75, to turn off the electric heat.

At this point it is well to point out a difference between the concept of FIG. 1 and the embodiment of FIG. 3. In FIG. 1 the comparison is made directly between two measurements of temperature in the critical region. In FIG. 3 the comparison is made of the desired temperature and the actual temperature. However, the overall result is the same, since in either instance a redundant temperature sensing means is used to ensure the accuracy of a non-redundant one which is used to directly control an electric heater. This illustrates the alternate ways the invention may be carried out.

When the audio alarm 74 sounds, if someone comes to cure the problem it is often desirable to be able to temporarily disable the alarm for a period of time long enough to permit repairs or other appropriate action. This is done by pressing the push button of the audio alarm disable circuit 80. That circuit includes a blocking oscillator and counter which, for a measured length of time, pulls the voltage on conductor 81 down. The low voltage on conductor 81 will turn on the transistor 82 to light up the yellow light emitting diode 83. The yellow "caution" indication will warn that the alarm is disabled. The low voltage on conductor 81 will also, through isolating diode 84 and transistor 71 turn off the audio alarm 72 and red LED 73. Thus, the yellow "caution" indication has been substituted for the red "danger" signal.

However, it is important to note that, when the audio alarm 72 is disabled, the shut down bus 75 is unaffected because of isolation supplied by diode 74. Thus, the electric heater resistor 30 can potentially still be turned off by an appropriate voltage applied to the inverting input of differential amplifier 47.

FIG. 4 shows the circuitry of the digital temperature display. The analog voltage from the output of voltage follower 43 of FIG. 3 is applied to analog to digital converter 88, which controls decoder driver 89, which controls the display device 90. The remainder of the circuitry need not be further explained since it will be apparent to those skilled in the art. The Figure is exemplary, for in many applications a display of tenths of a degree would be required.

Figure 5:
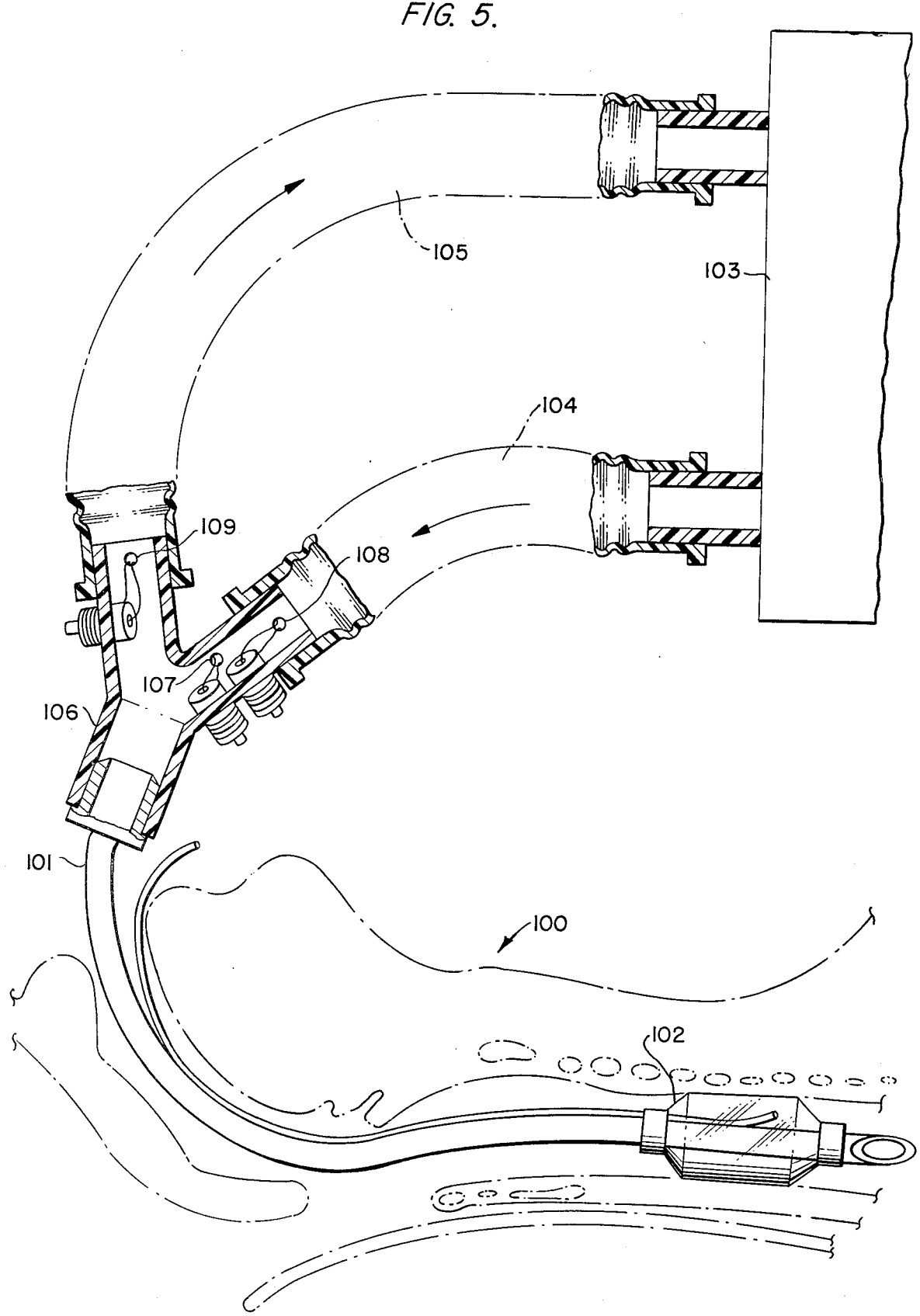
FIG. 5 shows how the present invention is utilized in an inhalation heater control system.

FIG. 5 illustrates an actual application of the invention. An unconscious patient 100 is being intubated with a tracheal tube 101, retained in place by cuff 102. The patient's lungs are ventilated by a respirator through inhalation hose 104, exhalation hose 105 and wye 106. Two thermistors, 107 and 108, in the inhalation passage, correspond to the thermistors 40 and 41 of FIG. 3. The thermistor 109 has a use, not relevant to the present invention, which is explained in the above-identified copending application.

Many other applications are evident.

What is claimed as the invention:

1. In combination with an electric heater for establishing an elevated temperature above ambient at a heated region spaced therefrom, and a temperature control system including a pair of sensors located adjacent each other at said region, signal comparing circuits respectively connected to said sensors for producing difference signals in response to deviation of the elevated temperature from a predetermined reference value and switching control means operatively connecting one of said signal comparing circuits to the heater for intermittent energization thereof tending to maintain the elevated temperature of the region at said predetermined reference value, the improvement residing in fail-safe assurance means comprising a third sensor located adjacent to the heater, shut-down control means connecting said third sensor to the switching control means for deenergizing and maintaining the heater deenergized in response to an excessive temperature differential between the heater and the heated region, and signal drift detection means connecting the other of the signal comparing circuits to the shut-down control means for alternatively deenergizing and maintaining the heater deenergized in response to bidirectional increase in the difference signals beyond a predetermined limit.

2. The improvement as defined in claim 1, including adjustable means connected to both of said signal comparing circuits for establishing said predetermined reference value.

3. The improvement as defined in claim 2, including alarm means connected to the signal drift detection means for producing an alerting output in response to said increase in the difference signals beyond said predetermined limit, means for selectively disabling the alarm means, and isolation coupling means connected to the alarm means for preventing disablement of the shut-down control means by the selective alarm disabling means.

4. The improvement as defined in claim 3, including indicating means connected to the switching control means for signifying said intermittent energization and maintained deenergization of the heater.

5. The combination of claim 4 wherein said heated region is within an inhalation hose of a respirator and said sensors are thermistors.

6. The improvement as defined in claim 1, including alarm means connected to the signal drift detection means for producing an alerting output in response to said increase in the difference signals beyond said predetermined limit, means for selectively disabling the alarm means and isolation coupling means connected to the alarm means for preventing disablement of the shut-down control means by the selectively disabling alarm means.

7. The improvement as defined in claim 1, including indicating means connected to the switching control means for signifying said intermittent energization and maintained deenergization of the heater.

8. The combination of claim 1 wherein said heated region is within an inhalation hose of a respirator and said sensors are thermistors.

* * * * *